(12) United States Patent
Lee et al.

(10) Patent No.: US 11,499,127 B2
(45) Date of Patent: Nov. 15, 2022

(54) MULTI-LAYERED MICROFLUIDIC SYSTEMS FOR IN VITRO LARGE-SCALE PERFUSED CAPILLARY NETWORKS

(71) Applicant: The Regents of the University of California, Oakland, CA (US)

(72) Inventors: Abraham P. Lee, Irvine, CA (US); Tao Yue, Irvine, CA (US); Da Zhao, Irvine, CA (US); Xiaolin Wang, Shanghai (CN); Christopher C. Hughes, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 712 days.

(21) Appl. No.: 16/166,989

(22) Filed: Oct. 22, 2018

(65) Prior Publication Data
US 2019/0119619 A1 Apr. 25, 2019

Related U.S. Application Data

(60) Provisional application No. 62/575,296, filed on Oct. 20, 2017.

(51) Int. Cl.
*C12M 3/06* (2006.01)
*C12M 3/00* (2006.01)
(Continued)

(52) U.S. Cl.
CPC ............ *C12M 23/16* (2013.01); *B01L 3/5027* (2013.01); *B01L 3/502707* (2013.01);
(Continued)

(58) Field of Classification Search
CPC ................. C12M 23/16; B01L 2300/0874
See application file for complete search history.

(56) References Cited

U.S. PATENT DOCUMENTS 2,656,508 A 10/1953 Coulter
3,380,584 A 4/1968 Fulwyler
(Continued)

FOREIGN PATENT DOCUMENTS

GB 2395196 5/2004
WO WO2007120240 A2 10/2007
(Continued)

OTHER PUBLICATIONS

International Search Report for PCT Application No. PCT/US17/55984 dated Dec. 14, 2017.
(Continued)

*Primary Examiner* — Jonathan M Hurst
(74) *Attorney, Agent, or Firm* — Nguyen Target LLC

(57) ABSTRACT

A multi-layered microfluidic system featuring tissue chambers for cells in a first layer and a plurality of medium channels for culture medium in a second layer. The tissue chambers fluidly connect to the medium channels such that media flows from the medium channels to the tissue chambers, forming large-scale perfused capillary networks. The capillary networks can undergo angiogenesis and vertical anastomosis. The multi-layered configuration of the system of the present invention allows for flexibility in design.

5 Claims, 11 Drawing Sheets
(11 of 11 Drawing Sheet(s) Filed in Color)

(51) Int. Cl.
    B01L 3/00     (2006.01)
    C12M 1/00     (2006.01)

(52) U.S. Cl.
    CPC .............. *C12M 3/00* (2013.01); *C12M 23/34*
         (2013.01); *C12M 29/00* (2013.01); *B01L*
              *2300/0816* (2013.01); *B01L 2300/0874*
         (2013.01); *B01L 2300/0887* (2013.01); *C12M*
              *23/26* (2013.01); *C12M 23/58* (2013.01)

(56)                References Cited

U.S. PATENT DOCUMENTS

| | | | |
|---|---|---|---|
| 4,009,435 | A | 2/1977 | Hogg |
| 5,465,582 | A | 11/1995 | Bliss et al. |
| 8,263,023 | B2 | 9/2012 | Le Vot et al. |
| 8,357,528 | B2 * | 1/2013 | Vacanti ................ C12N 5/0062 |
| | | | 435/284.1 |
| 8,365,311 | B2 | 1/2013 | Nawarathna |
| 8,927,040 | B2 | 1/2015 | Brand et al. |
| 9,176,504 | B2 | 11/2015 | Chiou et al. |
| 2002/0182654 | A1 | 12/2002 | Jing et al. |
| 2004/0234588 | A1 | 11/2004 | Lu et al. |
| 2005/0015001 | A1 | 1/2005 | Lec et al. |
| 2005/0106064 | A1 | 5/2005 | Laurell et al. |
| 2005/0272039 | A1 | 12/2005 | Yasuda |
| 2005/0272096 | A1 | 12/2005 | Clague et al. |
| 2006/0051329 | A1 | 3/2006 | Lee et al. |
| 2006/0177815 | A1 | 8/2006 | Soh et al. |
| 2007/0264320 | A1 | 11/2007 | Lee et al. |
| 2008/0038807 | A1 | 2/2008 | Pommersheim |
| 2008/0241875 | A1 | 10/2008 | Hwang et al. |
| 2009/0042310 | A1 | 2/2009 | Ward et al. |
| 2009/0068170 | A1 | 3/2009 | Weitz et al. |
| 2009/0075390 | A1 | 3/2009 | Linder et al. |
| 2009/0286300 | A1 | 11/2009 | Le Vot et al. |
| 2009/0298191 | A1 | 12/2009 | Whitesides et al. |
| 2011/0059556 | A1 | 3/2011 | Strey et al. |
| 2011/0086352 | A1 | 4/2011 | Bashir et al. |
| 2011/0285042 | A1 | 11/2011 | Viovy et al. |
| 2012/0034155 | A1 | 2/2012 | Hyde et al. |
| 2012/0107912 | A1 | 5/2012 | Hwang et al. |
| 2012/0196288 | A1 | 8/2012 | Beer |
| 2013/0078163 | A1 | 3/2013 | Chung et al. |
| 2013/0154671 | A1 | 6/2013 | Lee et al. |
| 2013/0171628 | A1 | 7/2013 | Di Carlo et al. |
| 2013/0210649 | A1 | 8/2013 | McKnight et al. |
| 2014/0011291 | A1 | 1/2014 | Patel et al. |
| 2014/0068797 | A1 | 3/2014 | Doudna et al. |
| 2014/0076430 | A1 | 3/2014 | Miller et al. |
| 2015/0018226 | A1 | 1/2015 | Hansen et al. |
| 2015/0377861 | A1 * | 12/2015 | Pant ...................... C12M 25/14 |
| | | | 506/9 |
| 2016/0033378 | A1 | 2/2016 | Husain et al. |
| 2016/0123858 | A1 | 5/2016 | Kapur et al. |
| 2016/0202153 | A1 | 7/2016 | Gadini et al. |
| 2016/0340631 | A1 * | 11/2016 | Wang .................. C12N 5/0693 |
| 2017/0014449 | A1 | 1/2017 | Bangera et al. |
| 2017/0128940 | A1 | 5/2017 | Amini et al. |
| 2017/0145169 | A1 | 5/2017 | Oakey et al. |
| 2017/0183722 | A1 | 6/2017 | Link |
| 2018/0030515 | A1 | 2/2018 | Regev et al. |
| 2018/0078940 | A1 | 3/2018 | Lee et al. |

FOREIGN PATENT DOCUMENTS

| | | |
|---|---|---|
| WO | WO2015157567 A1 | 10/2015 |
| WO | WO2016040476 A1 | 3/2016 |
| WO | WO2016126871 A2 | 8/2016 |
| WO | WO2017070169 A1 | 4/2017 |

OTHER PUBLICATIONS

International Search Report for PCT Application No. PCT/US18/56852 dated Jan. 11, 2019.
Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam me. 2010.
International Search Report for PCT Application No. PCT/US2016/056683 dated Dec. 27, 2016.
Stinson et al., Genes Expressed in the Male Gametophyte of Flowering Plants and Their Isolation, 1987, Plant Physiol., 83, 442-447.
Mazutis, L. et al., Lab on a Chip, vol. 9, pp. 2665-2672 (2009).
Simon, M.G. et al., Label-Free Detection of DNA Amplification in Dropletsusing Electrical Mpedance, 15th International Conference on Miniaturized Systems for Chemistry and Life Sciences 2011 (MicroTAS 2011), pp. 1683-1685 (Year: 2011).
Marsh et al. Room temperature ionic liquids and their mixtures—a review. Fluid Phase Equilibria 219 (2004) 93-98.
Oh, Woon Su, "Synthesis and applications of imidazolium-based ionic liquids and their polymer derivatives" (2012). Doctoral Dissertations. 1958 http://scholarsmine.mst.edu/doctoral_dissertations/1958.
Baret et al., "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.
Macosko et al., "Highly Parallel Genome-wide Expression Profiling of Individual Cells Using Nanoliter, Droplets," Cell, vol. 161, No. 5, pp. 1202-1214, May 2015.
International Search Report for PCT Application No. PCT/US18/36962 dated Aug. 30, 2018.
International Search Report for PCT Application No. PCT/US18/36952 dated Sep. 18, 2018.
Inexpensive Droplet-Based Microfluidic Platform. CIDAR lab. https://www.youtube.com/watch?v=aHvfEOlh_b4.
Kamalakshakurup et al. High-efficiency single cell encapsulation and size selective capture of cells in picoliter droplets based on hydrodynamic micro-vortices. Lab Chip, 2017, 17, 4324-4333.
Brouzes, Eric, et al. "Droplet microfluidic technology for single-cell high-throughput screening." Proceedings of the National Academy of Sciences 106.34 (2009): 14195-14200.
S. I. Rubinow and J. B. Keller, "The transverse force on a spinning sphere moving in a viscous fluid," J. Fluid Mech., vol. 11, No. 03, p. 447, Nov. 1961.
Murata et al., Electrochemical single-cell gene-expression assay combining dielectrophoretic manipulation with secreted alkaline phosphatase reporter system, 2009, Biosensors and Bioelectronics, 25, 913-919.
International Search Report for PCT Application No. PCT/US18/55722 dated Feb. 6, 2019.
Doria, Arlene et al., "Rapid blood plasma separation with air-liquid cavity acoustic transducers", 15th International conference on miniaturized systems for chemistry and life sciences, Oct. 2-6, 2011, pp. 1882-1884.
Lee, Abraham P. et al. , "Microfluidic air-liquid cavity acoustic transducers for on-chip integration of sample preparation and sample detection", Journal of laboratory automation, Dec. 2010, vol. 15, No. 6, pp. 449-454.
International Search Report Issued for PCT Application No. PCT/US2013/042735 dated Nov. 28, 2013.
J. Kim, M. Chung, S. Kim, D. H. Jo, J. H. Kim, and N. L. Jeon, "Engineering of a Biomimetic Pericyte-Covered 3D Microvascular Network," Pios One, vol. 10, p. e0133880, 2015.
X. Wang, D. T. T. Phan, A. Sobrino, S. C. George, C. C. W. Hughes, and A. P. Lee, "Engineering anastomosis between living capillary networks and endothelial cell-lined microfluidic channels," Lab on a Chip, vol. 16, pp. 282-290, 2016.

* cited by examiner

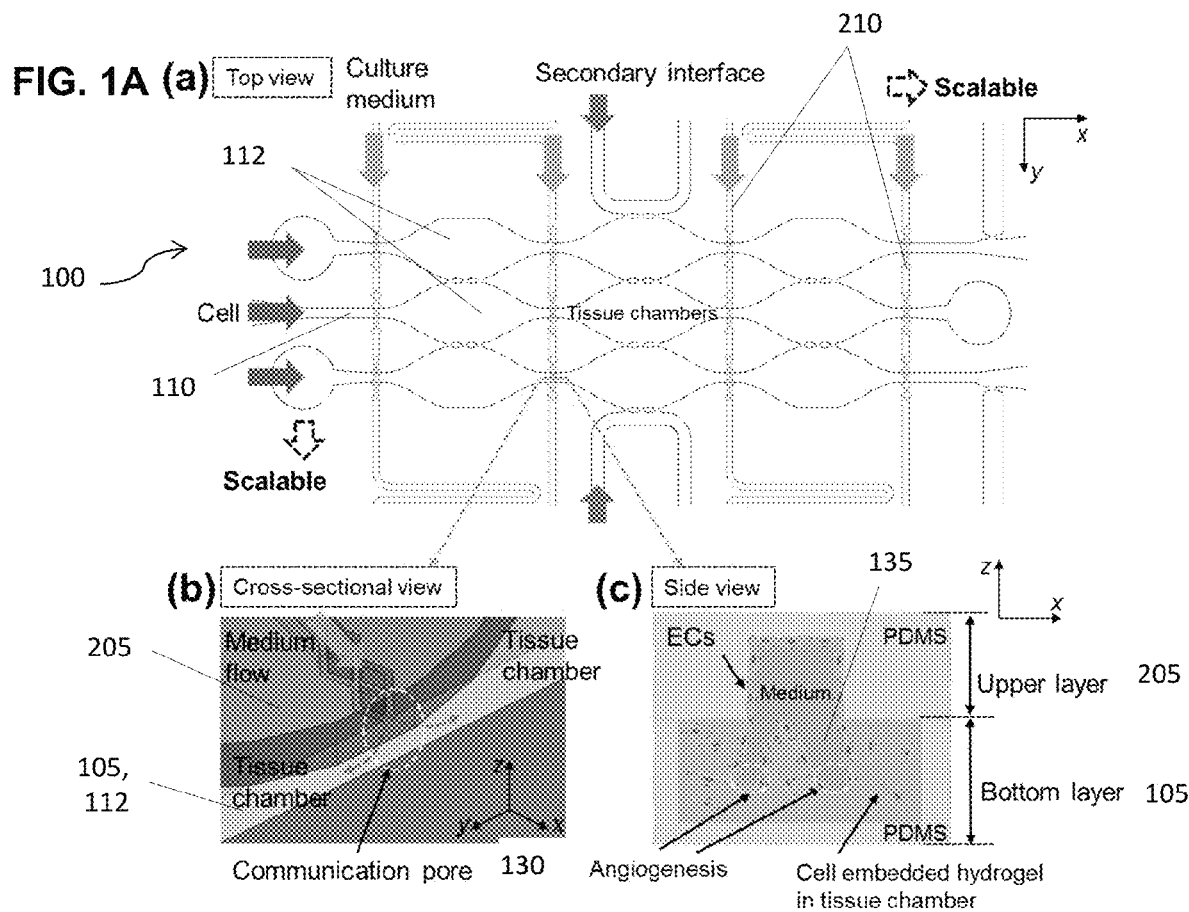
FIG. 1A
FIG. 1B
FIG. 1C
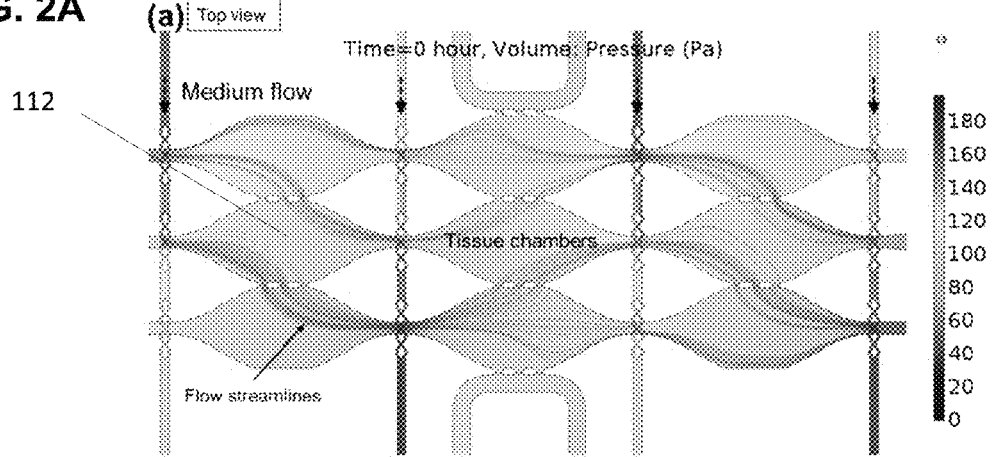
FIG. 2A
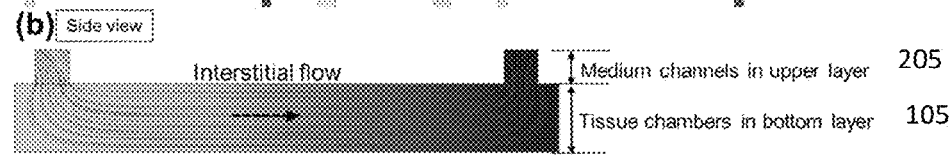
FIG. 2B

FIG. 7E  FIG. 7F

MULTI-LAYERED MICROFLUIDIC SYSTEMS FOR IN VITRO LARGE-SCALE PERFUSED CAPILLARY NETWORKS

CROSS REFERENCE

This application claims priority to U.S. Patent Application No. 62/575,296, filed Oct. 20, 2017, the specifications of which is incorporated herein in their entirety by reference.

GOVERNMENT SUPPORT

This invention was made with government support under Grant No. UH3 TR00048 awarded by NIH. The government has certain rights in the invention.

FIELD OF THE INVENTION

The present invention relates to microfluidic devices for tissue culture, more particularly to microfluidic devices for developing three-dimensional large-scale capillary networks.

BACKGROUND OF THE INVENTION

The vascular network of the circulatory system plays a vital role in maintaining homeostasis of the human body. In vitro systems, such as organs-on-a-chip attempt to mimic the characteristics and functions of in vivo organs by, for example, integrating large-scale microvasculature networks.

Previously constructed perfused capillary networks feature anastomosis between capillary networks and microfluidic channels. However, these have a single-layer configuration and have limited scalability and positioning flexibility (e.g., positioning of the capillary networks).

It was surprisingly discovered that a two-layer configuration, which separates the culture medium and tissue chambers, allows for formation of large-scale perfused capillary networks. The two-layer configuration also provides improved scalability and improved positioning flexibility.

SUMMARY OF THE INVENTION

The present invention features a multi-layered microfluidic system. The system of the present invention comprises tissue chambers for cells in a first layer and a plurality of channels for culture medium in a second layer. Media flows through the tissue chambers, forming large-scale perfused capillary networks. As described below, angiogenesis and vertical anastomosis have been successfully achieved in systems of the present invention. The disclosure herein demonstrates multiple capillary chambers connected to each other by perfusion of blood through the interconnected capillary vessels.

The multi-layered configuration of the system of the present invention allows for flexibility in design. For example, the thickness, density, and shape of the tissue chambers or medium channels can be designed independently, allowing, for example, the tissue chambers to be packed densely while medium supply can flow through multiple tissues.

In some embodiments, the layer with the culture medium channels (second layer) comprises tissue chambers as well. This allows for the creation of a multi-layer vascular tissue connection construct.

The present invention features microfluidic systems. In some embodiments, the microfluidic system comprises a first layer comprising one or a plurality of cell channels embedded therein, each cell channel comprising one or more a plurality of tissue chambers for housing cells; a second layer comprising one or a plurality of medium channels embedded therein, the second layer is bonded to the first layer; and one or a plurality of communication pores that fluidly connect a tissue chamber with a medium channel such that cells in the tissue chamber receive media from the medium channel.

In some embodiments, the second layer is bonded atop the first layer. In some embodiments, the second layer is bonded below the first layer.

The cell channels may be aligned in an x-direction, and the medium channels are aligned in a y-direction. In some embodiments, the cell channels are aligned in a y-direction, and the medium channels are aligned in an x-direction.

In some embodiments, one or more tissue chambers of one or more cell channels (e.g., a first cell channel) are fluidly connected to one or more tissue chambers of one or more cell channels (e.g., a second cell channel)

The tissue chambers may comprise a matrix composition, e.g., a hydrogel, e.g., a hydrogel comprising fibrin. The cell may comprise one population of cells. In some embodiments, the cells comprise two or more different populations of cells. In some embodiments, the cells comprise stem cells, inducible pluripotent stem cell-derived cells, progenitor cells, the like, or terminally differentiated cells, or a combination thereof. In some embodiments, the cells are derived from blood, cardiac tissue, skeletal muscle tissue, liver tissue, pancreatic tissue, lung tissue, bone tissue, umbilical cord tissue, endothelial tissue, central nervous system tissue, gastrointestinal system tissue, endocrine tissue or cells, paracrine cells, enzyme secreting cells, progenitors thereof, the like, or a combination thereof.

In some embodiments, the cells undergo angiogenesis. As a non-limiting example, the cells may undergo angiogenesis to form perfused capillary networks. In some embodiments, an anastomosis may be formed between multiple channels. As a non-limiting example, a vertical anastomosis may join a first channel (e.g. a cell-containing channel) to a second channel (e.g. a medium-providing channel) such that a fluid medium may flow vertically between the two channels. As another non-limiting example, a horizontal anastomosis may join two channels or tissue chambers (e.g. two cell-containing tissue chambers) in the same layer so to allow for medium flow and cell interactions between the two channels or tissue chambers. As a further non-limiting example, joining two tissue chambers by a horizontal anastomosis may allow for microfluidic modelling of multiple tissue type or multiple organ type systems.

In some embodiments, the medium channel is fluidly and operatively connected to a pump. In some embodiments, the microfluidic pump comprises a pneumatic pump. In some embodiments, flow of the media in the medium channel is pressure-driven. In some embodiments, media is delivered from the medium channels to generate interstitial flow across the tissue chambers. Interstitial flow may refer to a convective flow through a tissue extracellular matrix or a gel which is loaded into a tissue chamber. In preferred embodiments, the interstitial flow may be driven by a pressure difference across the tissue chamber. As a non-limiting example, different pressures applied to different medium channels may provide for various pressure profiles through the tissue chambers. As an additional non-limiting example, the pressures applied to different medium channels may provide for multiple tissue chambers which have the same pressure difference and pressure profile so as to allow for parallel experiments on the same chip. In some embodiments, the cell channels comprise loading ports for loading cells into the tissue chambers. In some embodiments, media is supplied through the medium channels under a stable pressure drop from inlet to outlet.

In some embodiments, the microfluidic system (e.g., for forming a perfused capillary network) comprises a first layer comprising a plurality of cell channels embedded therein, each cell channel having a plurality of tissue chambers disposed along said cell channel, the tissue chamber being configured for housing cells, wherein the tissue chamber has a width greater than a width of the cell channel, wherein the cell channels are arranged so as to be in parallel with each other and so that the tissue chambers of one cell channel is aligned with the tissue chambers of the neighboring cell channel, wherein the tissue chambers of one cell channel is fluidly connected to the tissue chambers of the neighboring cell channel; a second layer comprising a plurality of medium channels embedded therein, the medium channels being aligned in parallel with each other, wherein the second layer is bonded to the first layer such that the medium channels are perpendicular to the cell channels; and a plurality of communication pores, each communication pore being disposed at each intersection of the medium channels and the cell channels such that the communication pore fluidly connects the medium channel to the cell channel such that cells in the tissue chambers receive media from the medium channel. The cell channels may be aligned in an x-direction, the medium channels are aligned in a y-direction, and the communication pores are disposed in a z-direction. The media may be delivered from the medium channels to the cell channels via the communication pores to generate interstitial flow across the tissue chambers.

The present invention also features methods, e.g., methods of producing a perfused capillary network. In some embodiments, the method comprises providing a microfluidic system according to the present invention; loading cells and a cell matrix into the tissue chambers; curing the cell matrix; and introducing culture media into the medium channels, wherein after a period of time, capillaries form connected networks.

In some embodiments, the period of time is at least 5 days. In some embodiments, the period of time is at least 10 days. In some embodiments, the matrix composition comprises a hydrogel, e.g., a fibrin hydrogel.

In some embodiments, the cells comprise one population of cells. In some embodiments, the cells comprise two or more different populations of cells. In some embodiments, the cells comprise stem cells, inducible pluripotent stem cell-derived cells, progenitor cells, or terminally differentiated cells. In some embodiments, the cells are derived from blood, cardiac tissue, skeletal muscle tissue, liver tissue, pancreatic tissue, lung tissue, bone tissue, umbilical cord tissue, endothelial tissue, central nervous system tissue, gastrointestinal system tissue, endocrine tissue or cells, paracrine cells, enzyme secreting cells, progenitors thereof, or a combination thereof.

In some embodiments, the cells undergo angiogenesis. In some embodiments, the cells undergo anastomosis.

In some embodiments, media is delivered from the medium channels to generate interstitial flow across the tissue chambers. In some embodiments, media is supplied through the medium channels under a stable pressure drop from inlet to outlet.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawings will be provided by the Office upon request and payment of the necessary fee.

The features and advantages of the present invention will become apparent from a consideration of the following detailed description presented in connection with the accompanying drawings in which:

FIG. 1A shows a schematic representation (a top view) of a microfluidic system of the present invention. The system features a two-layered microfluidic device with scalable channels for culture medium in a first layer (e.g., upper layer) and scalable chambers for tissue growth in a second layer (e.g., bottom layer).

FIG. 1B shows a cross-sectional view of a communication pore of the system in FIG. 1A.

FIG. 1C shows a side view of the communication pore of the system of FIG. 1A.

FIG. 2A shows a numerical simulation of medium flow in a system of the present invention (a top view showing the interstitial flow for angiogenesis and anastomosis).

FIG. 2B shows a side view of one tissue chamber of the system of FIG. 2A.

FIG. 7E shows a top-view drawing of a crossover region between a first channel and a second channel, the crossover region featuring a communication pore formed by two non-intersecting branch channels.

FIG. 7F shows a top-view drawing of a crossover region between a first channel and a second channel, the crossover region featuring a communication pore formed by three non-intersecting branch channels.

DETAILED DESCRIPTION OF THE INVENTION

Figure 3A:
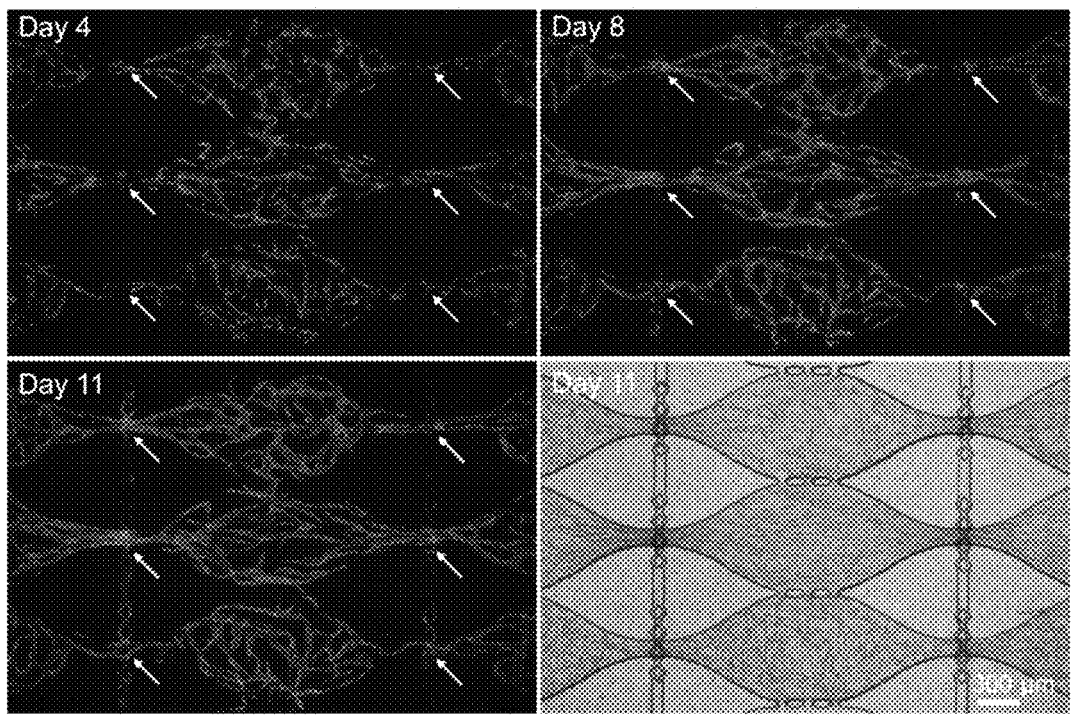
FIG. 3A shows the development of large-scale capillary networks (angiogenesis in tissue chambers).

In some embodiments, the present invention features a multi-layered microfluidic system. The system of the present invention comprises tissue chambers for cells in a first layer and a plurality of channels for culture medium in a second layer. Media flows through the tissue chambers, forming large-scale perfused capillary networks. In some embodiments, the layer with the culture medium channels (second layer) also comprises tissue chambers. This may allow for the creation of a multi-layer vascular tissue connection construct.

Compared to single-layered microfluidic devices, the multi-layered configuration of the present invention, wherein channels for culture medium and chambers for tissues are separated into different layers, provides more flexibility and scalability for design and fabrication. Also, the depth of the medium channels and tissue chambers can be modulated independently, which helps provide a constant flow profile when changing the thickness of the tissues. And, the multi-layered configuration helps provide more space to increase the density of tissue chambers and medium channels.

Referring to FIG. 1A, FIG. 1B, and FIG. 1C, the system (100) of the present invention comprises a first layer (105) (e.g., a cell layer) bonded to a second layer (205) (e.g., a media layer). In some embodiments, the second layer (205) is bonded or positioned atop the first layer (105). In some embodiments, the second layer (205) is bonded or positioned below the first layer (105). The first layer (105) comprises embedded cell channels (110) with inlets and outlets. The cell channels (110) feature tissue chambers (112) for housing cells and/or tissue. In some embodiments, the cell channels (110), e.g., tissue chambers (112), comprise a cell matrix or scaffold material. The cell matrix may, for example, comprise a hydrogel (e.g., a fibrin gel). However, the present invention is not limited to a hydrogel or a fibrin-based hydrogel. The first layer (105) may comprise one or a plurality of cell channels (110), e.g., 2, 3, 4, 5, 6, 7, 8, 9, 10, 11, 12, etc. The cell channels (110) may comprise one or a plurality of tissue chambers (112), e.g., 2, 3, 4, 5, etc. The example shown in FIG. 1A comprises three cell channels (110) each with three tissue chambers (112); however, the present invention is not limited to the configuration shown in FIG. 1A.

In one embodiment, the present invention features a microfluidic system (100). As a non-limiting example, the system may comprise: a first layer (105) comprising a first channel (110) therein, the first channel (110) fluidly connected to a plurality of tissue chambers (112) which are configured to house cells; a second layer (205) above or below the first layer (105), the second layer (205) comprising a second channel (210) therein; and a communication pore (130) forming a vertical anastomosis (135) between the first channel (110) and the second channel (210) in the crossover region (120). In a preferred embodiment, the first layer (105) may comprise a high density of tissue chambers (112).

According to one embodiment, the first channel (110) may comprise a cell-containing channel or a channel configured to contain or culture cells. As a non-limiting example, the first channel (110) may comprise a cell channel that is loaded with endothelial cells and fibroblasts mixed in fibrin gel. In a selected embodiment, cancer cells may be added to the gel to build a disease model. As a non-limiting example, at around day 3-5, the endothelial cells may form lumen to generate capillary network, and around day 5-7, the lumen may be enlarged and anastomosed, such that some endothelial cells will grow up to the communication pore (the crossover part of the medium channel and tissue channel) to form a good connection and seal between the medium channel and the capillary network. In some preferred embodiments, the cells may form a capillary network within the first channel (110).

According to another embodiment, the second channel (210) may comprise a medium channel or a channel configured to provide a fluid medium. In some embodiments, the medium channel may be used to deliver a cell culture medium to the cell and gel mixture. As a non-limiting example, from day 1 to day 5, the medium channel may primarily contain cell culture medium, and after day 5 or 7, some endothelial cells from the tissue chamber may grow up and adhere to the medium channel wall at the communication pore region. In a further non-limiting example, drugs may be delivered to the cells or tissue through the medium channel and anastomosed capillary network.

In one embodiment, the second channel (210) may comprise a first full-width region (212) and a second full-width region (212). In another embodiment, the second channel (210) may comprise a first branch point (214) at an end of the first full-width region (212), a second branch point (214) at an end of a second full-width region (212), and a node (230) between the two branch points (214). In yet another embodiment, the second channel (210) may comprise a plurality of branch channels (225) fluidly connecting the first branch point (214), the node (230), and the second branch point (214), wherein the branch channels (225) are disposed separately between the first branch point (214) and the node (230) and between the node (230) and the second branch point (214), and wherein the branch channels (225) recombine at each branch point (214) and at the node (230). In some embodiments, the second channel (210) may comprise a plurality of nodes (230) between the branch points (214).

Figure 7A:
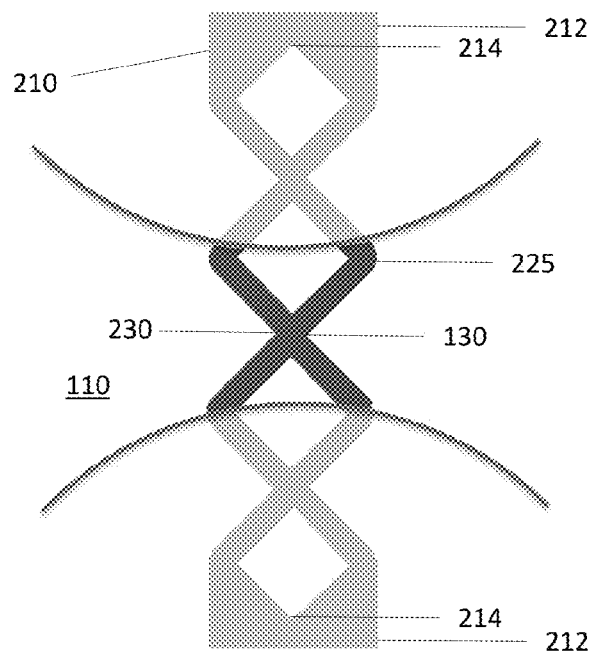
FIG. 7A shows a top-view drawing of a crossover region between a first channel and a second channel, the crossover region featuring a communication pore formed by two intersecting branch channels.
Figure 7B:
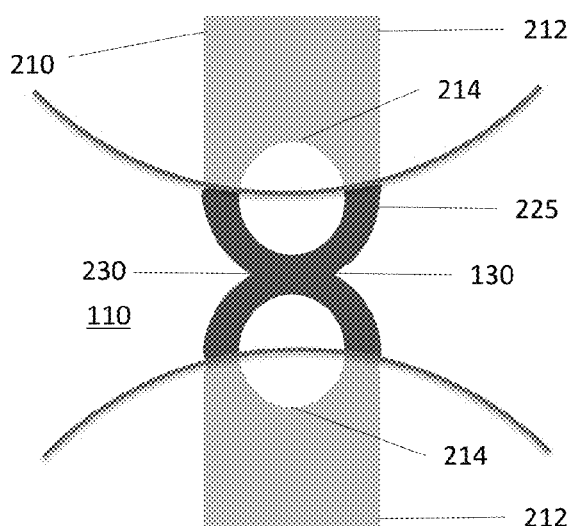
FIG. 7B shows a top-view drawing of a crossover region between a first channel and a second channel, the crossover region featuring a communication pore formed by two intersecting branch channels.
Figure 7C:
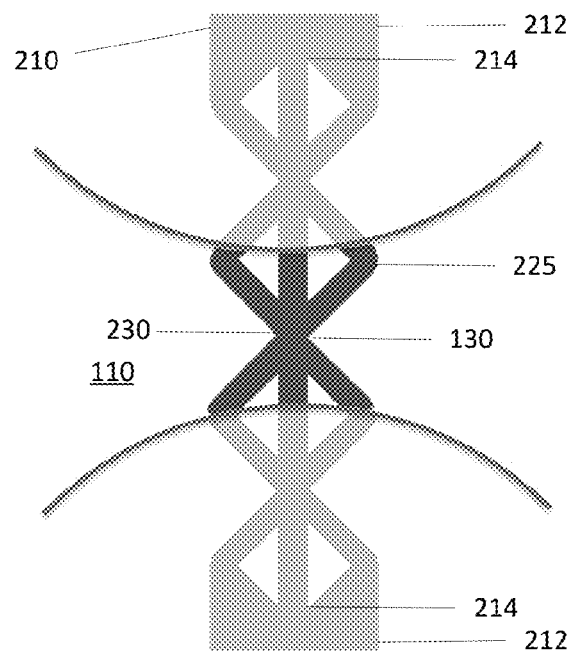
FIG. 7C shows a top-view drawing of a crossover region between a first channel and a second channel, the crossover region featuring a communication pore formed by three intersecting branch channels.
Figure 7D:
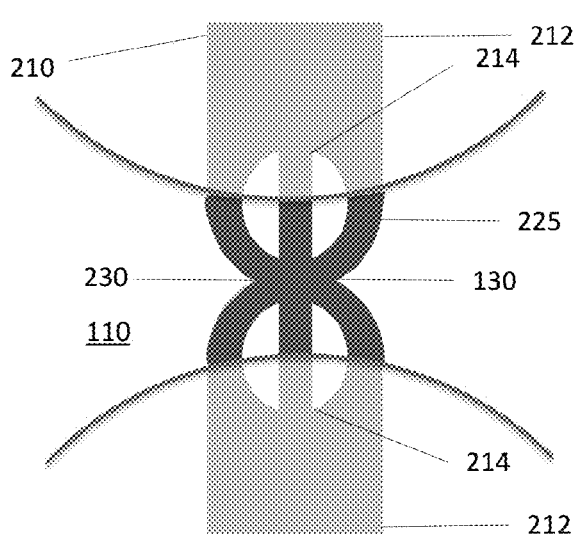
FIG. 7D shows a top-view drawing of a crossover region between a first channel and a second channel, the crossover region featuring a communication pore formed by three intersecting branch channels.
Figure 8:
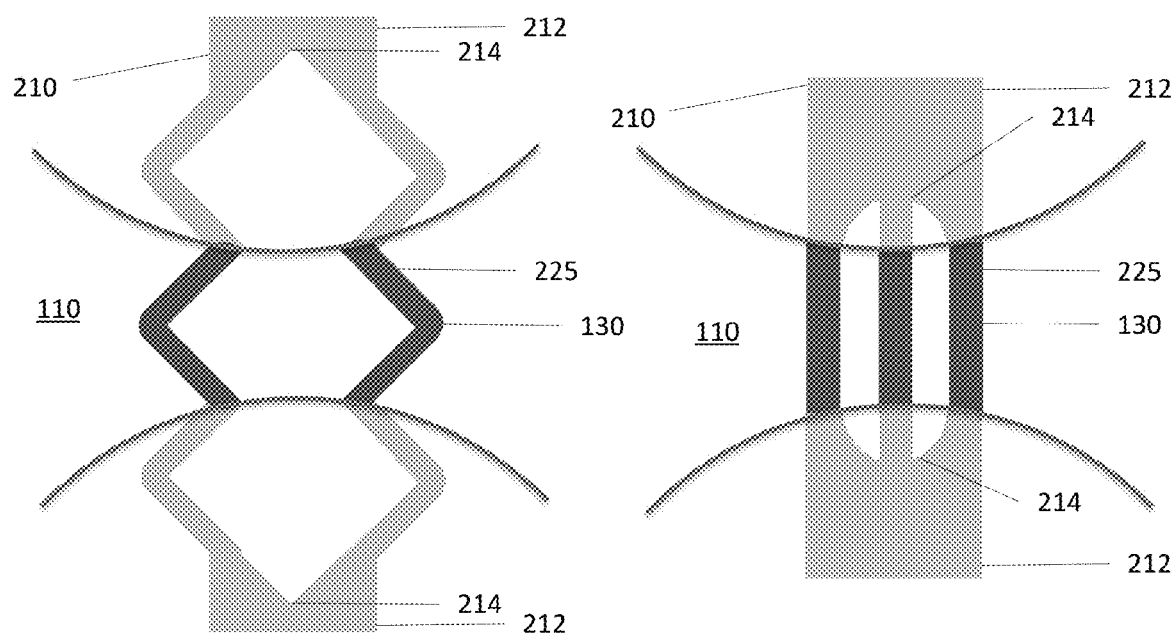
FIG. 8 shows illustrations of a modular microfluidic system of the present invention which is formed by combining by two polydimethylsiloxane (PDMS) layers. The system includes a medium channel module (a) (Upper layer) and a tissue chamber module (b) (Bottom layer). There are different channel designs used in these two modules. The layers can be stacked to form a two-layered device (c). Large scale perfused capillary networks (d) can be generated using different configurations.
Figure 8:
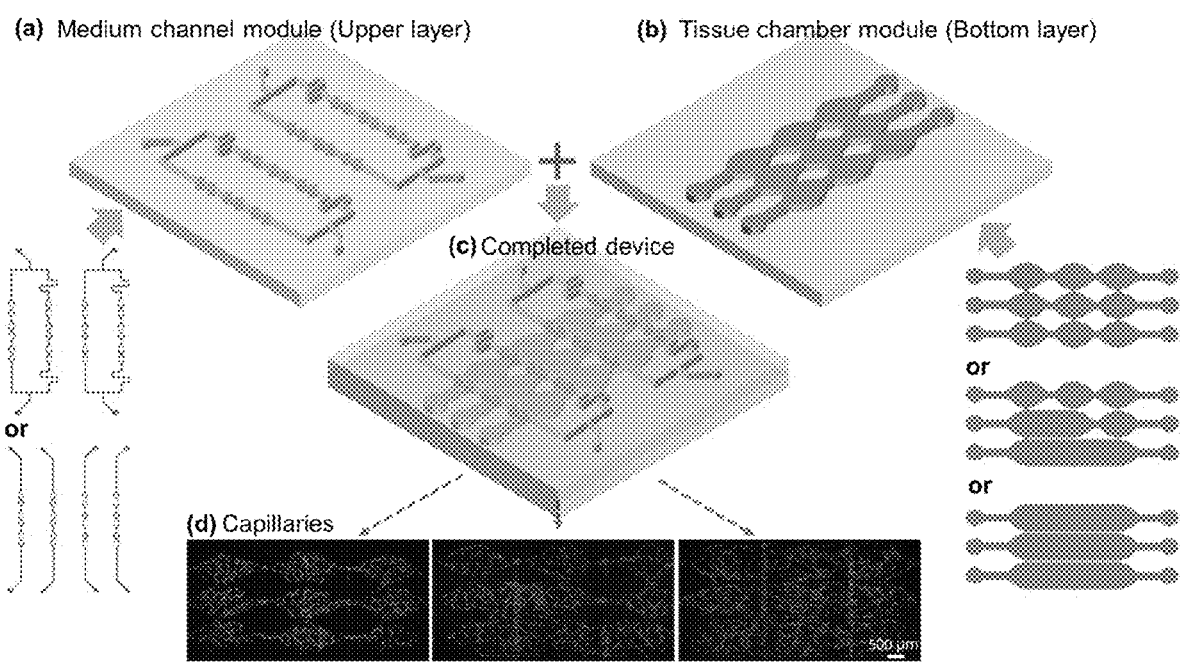
Figure 9:
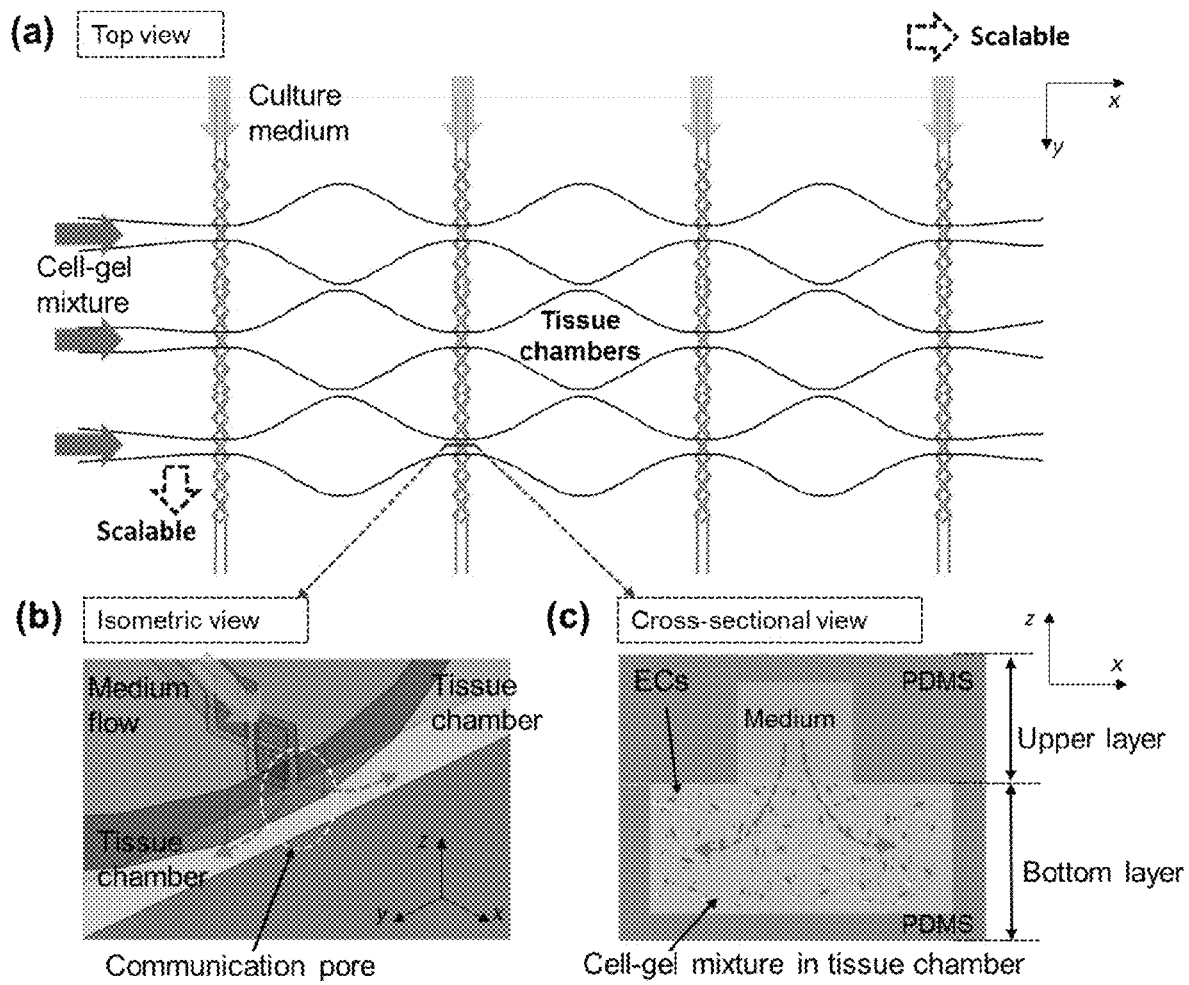
FIG. 9 shows a schematic drawing of a device of the present invention and the simulated flow conditions inside. A top view (a) of the device shows a layout with a 3×3 tissue matrix. Cell-embedded fibrin gels are loaded into bottom tissue chambers. Then the culture medium is supplied through upper medium channels. The isometric view (b) of a communication pore shows how the medium flows from the medium channel to the tissue chamber. The cross-sectional view (c) of the communication pore shows the distribution of the cells, gel and medium, as well as the flow direction of medium.
Figure 10A:
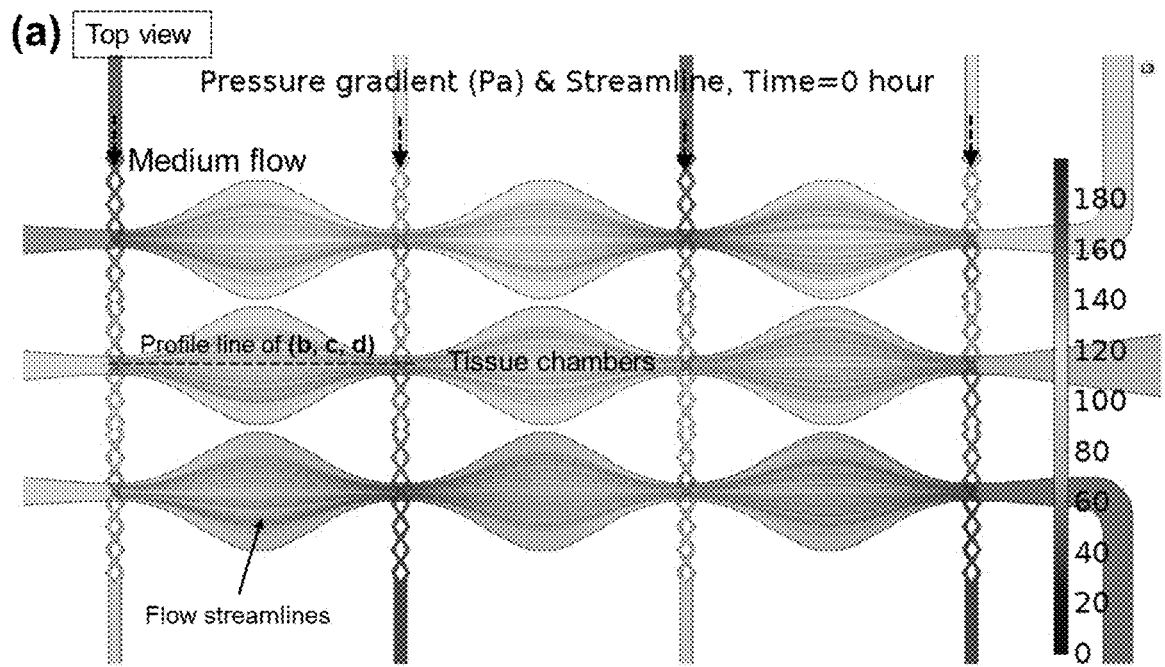
FIG. 10A shows a numerical simulation of medium flow in a system of the present invention which has walls separating the rows of tissue chambers (a top view showing the interstitial flow for angiogenesis and anastomosis).
Figure 10B:
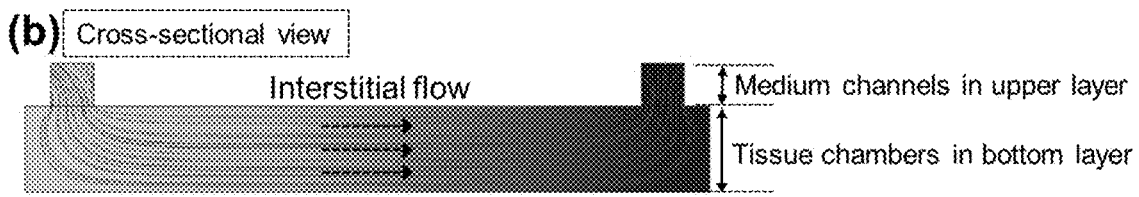
FIG. 10B shows a side view of one tissue chamber of the system of FIG. 10A.
Figure 10C:
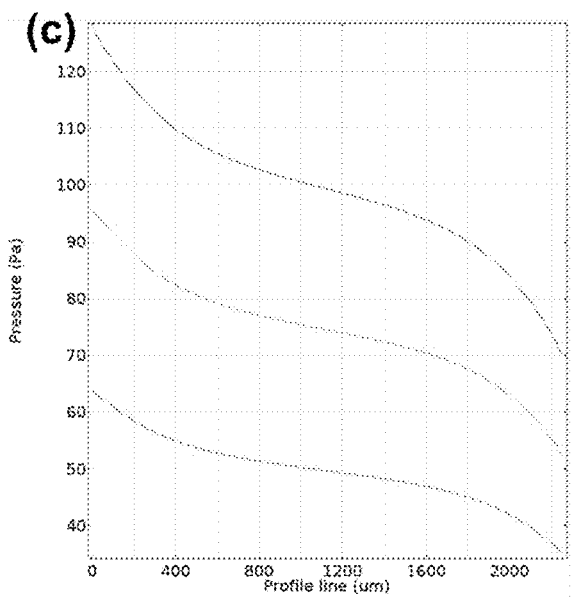
FIG. 10C shows a graph of the pressure drops within the tissue chambers and that chambers can have the same pressure profile even with different pressures.
Figure 10D:
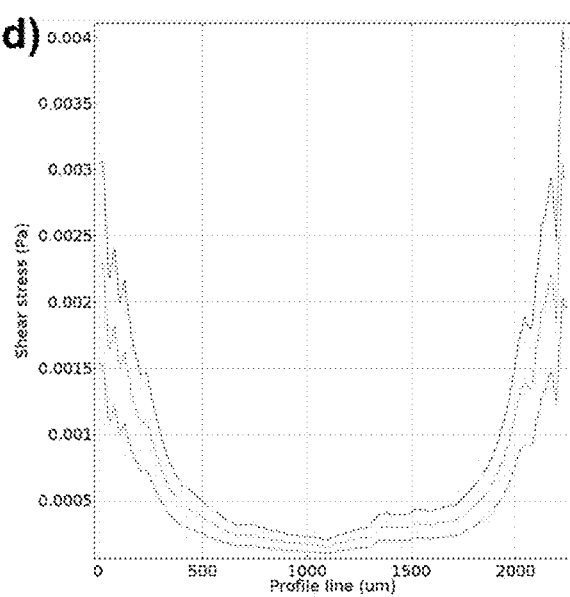
FIG. 10D shows a graph of the shear stress distribution across one tissue chamber. This illustrates that there is a higher shear stress near the communication pores, which may result in vessels with larger diameters.

In some embodiments, the system may feature a crossover region (120) in which the second channel (210) passes over or under the first channel (110). In a preferred embodiment, the crossover region (120) comprises the node (230) and the branch channels (225) but not the full-width regions (212) of the second channel (210). In another preferred embodiment, the crossover region (120) may comprise a plurality of branch channels (225) which do not intersect or comprise a node (230) within the crossover region (120) (See FIG. 7E and FIG. 7F).

In still another preferred embodiment, the second channel (210) may have a configuration at the crossover region (120) such that the channel maintains a flow rate and also has a narrow channel width such that there is a surface tension force which prevents a gel from passing from the first channel (110) into the second channel (210). In one embodiment, the communication pore (130) may be configured to prevent a gel from passing from the first channel (110) into the second channel (210). In other embodiments, the branch channels (225) may be narrow enough to prevent a gel from passing from the first channel (110) into the second channel (210). In still other embodiments, the communication pore (130) may be configured to provide for a flow of a liquid medium from the second channel (210) to the first channel (110). In one preferred embodiment, the branch channels (225) may be narrower than the full-width regions (212) of the second channel (210).

Figure 11:
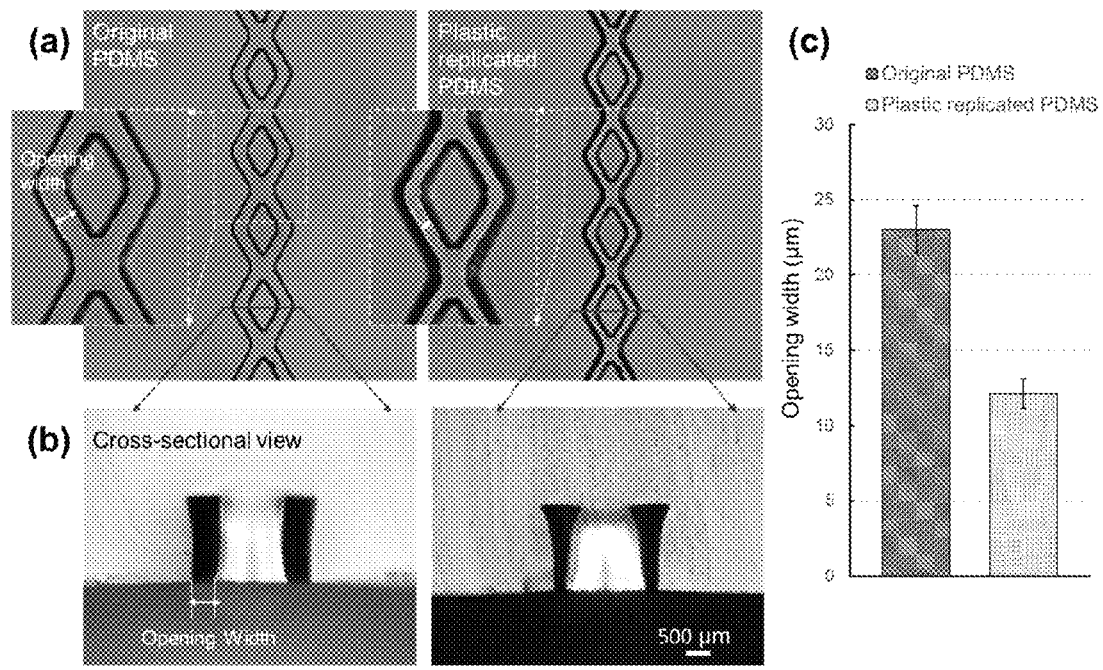
FIG. 11 shows the difference between branch channels formed in an original PDMS layer and a plastic replicated PDMS layer. The top views (a) of the channels show a narrowing of the opening width in the plastic replicated PDMS layer. The cross sectional views (b) show a tapered channel profile in the plastic replicated PDMS layer which has a wide base and a narrow opening width. A graph of the opening widths (c) shows that the tapering of the channel in the plastic replicated PDMS layer can significantly reduce the opening width as compared to the channel in the original PDMS layer.
Figure 12:
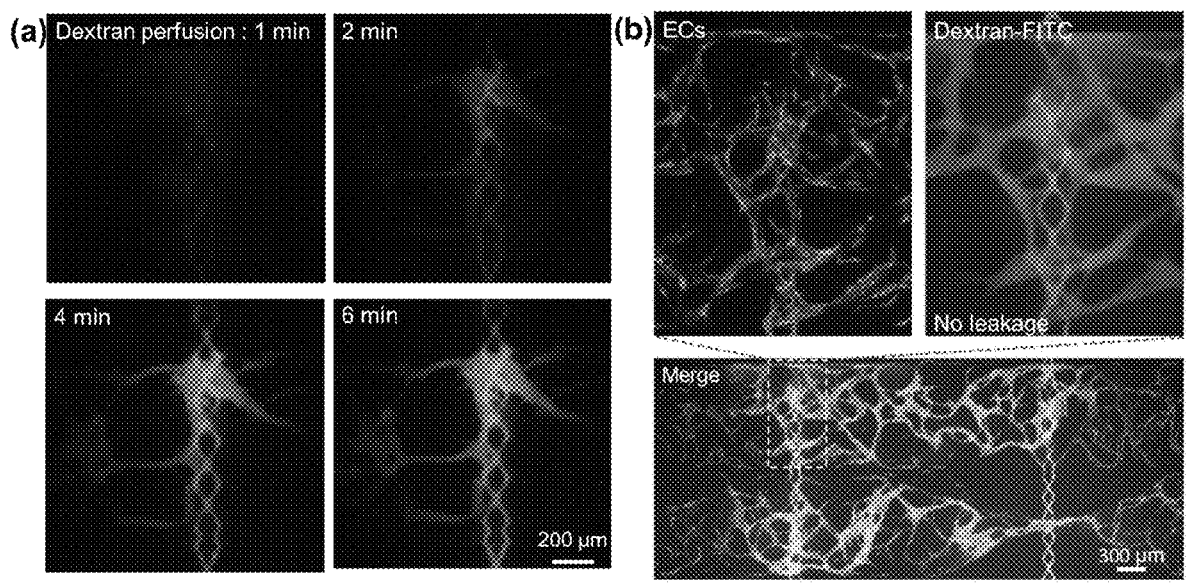
FIG. 12 shows a demonstration of the leak-free sealing at the communication pores using images of dextran perfusion.
Figure 13A:
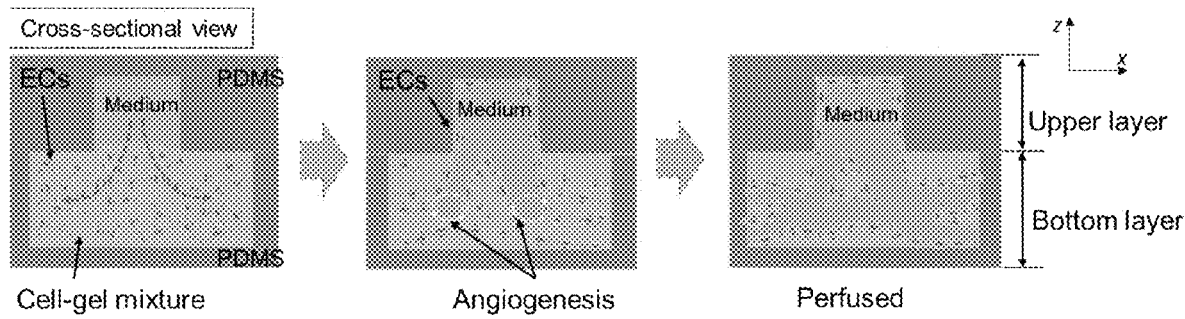
FIG. 13A shows schematic drawings of cell growth at the communication pores, wherein the cells in the cell-gel mixture undergo angiogenesis to form a perfused capillary network. Some of the cells may migrate into the medium channel and line the walls of the medium channel.
Figure 13B:
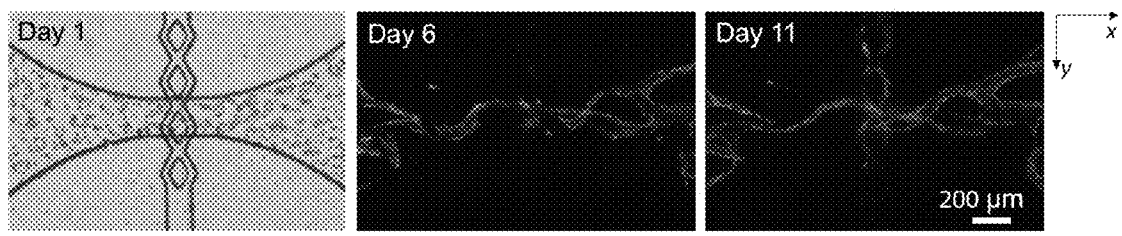
FIG. 13B shows experimental results illustrating cell growth at the communication pores on day 1, day 6, and day 11.
Figure 13C:
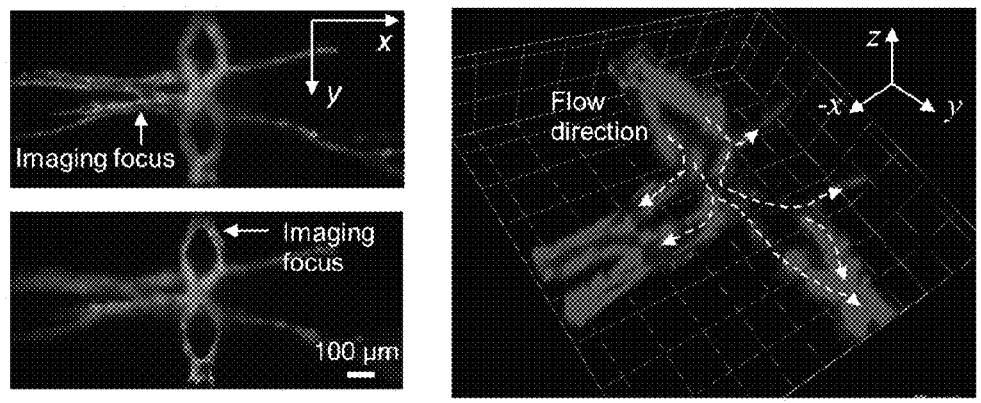
FIG. 13C shows experimental results illustrating cell growth and vertical anastomosis formation at a communication pore.
Figure 14:
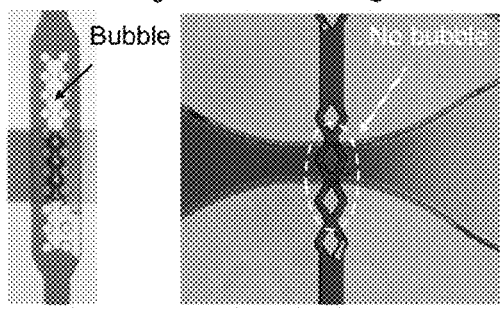
FIG. 14 shows different channel designs for the crossover region and how the new design prevents bubble formation in the communication pore better than the previous design.
Figure 15:
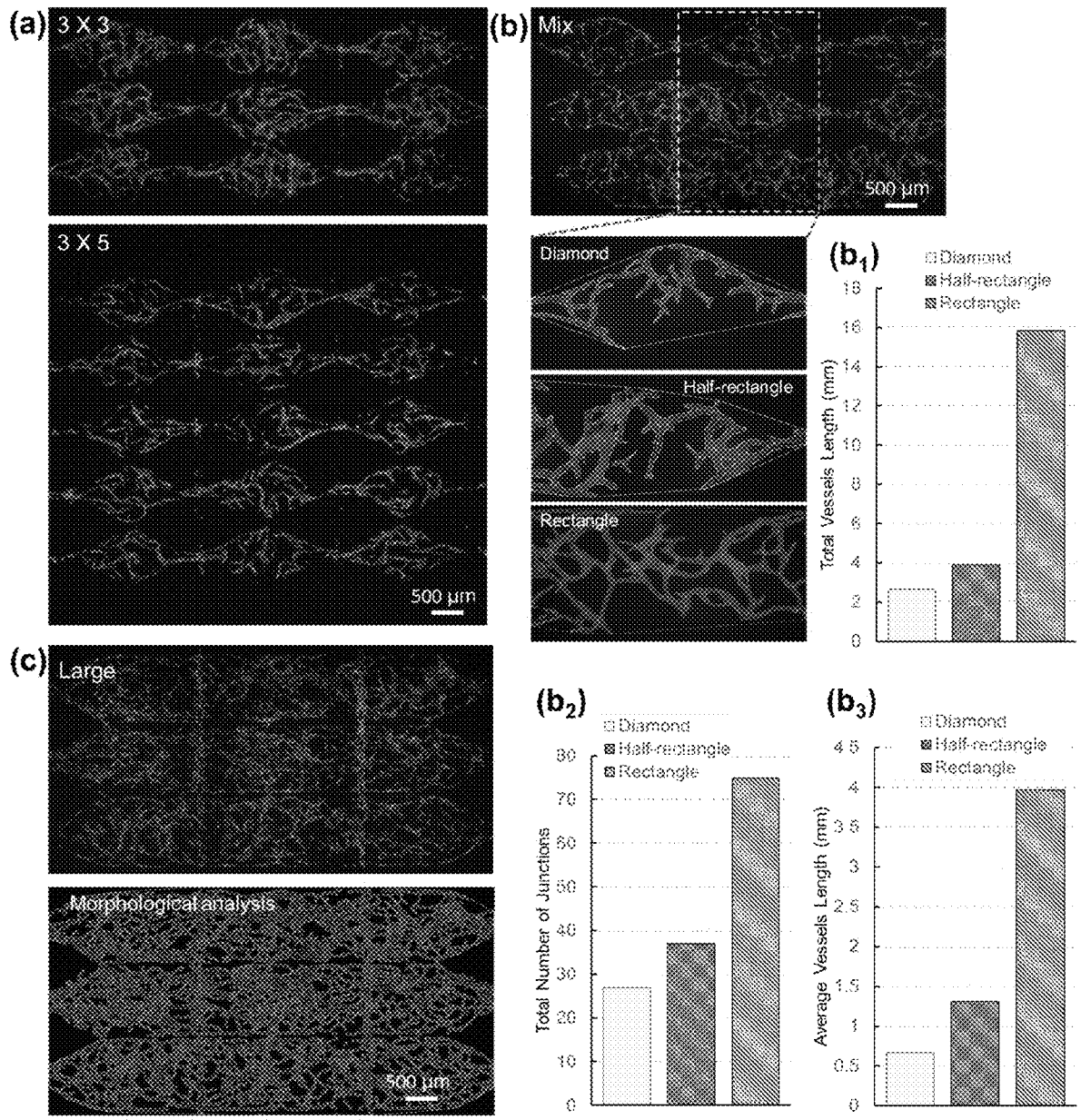
FIG. 15 shows various large-scale capillary networks. Images (a) of 3×3 and 3×5 grids of tissue chambers show the extensive formation of capillary networks. A device with a mix (b) of diamond, half-rectangle and rectangle shaped tissue chambers allows for direct comparison of the total vessel length (b1), total number of junctions (b2), and the average vessel length (b3). Rectangle shaped tissue chambers (c) were shown to generate longer and denser capillaries and have lower shear stress as compared to diamond shaped tissue chambers.

In one embodiment, the second channel (210) may be formed using a method of plastic replication which provides a channel with a small opening width. (See FIG. 11) As a non-limiting example, the method may comprise forming an original polydimethylsiloxane (PDMS) channel using an original mold, filling the original PDMS channel with a plastic such as a polyurethane (e.g. Smooth-cast 310) to form a plastic replicated mold, and using the plastic replicated mold to form a plastic replicated PDMS channel. The method of forming a plastic replicated PDMS channel may cause a lack of fidelity to the original pattern. In many cases, this lack of fidelity may be undesirable but, in this instance, it may be advantageous. As a non-limiting example, the method of plastic replication may provide a channel with tapered sides such that the channel has a base which is wider than an opening width. Without wishing to limit the invention to any particular theory or mechanism, it is believed that a channel geometry having tapered sides and a base which is wider than the opening width may allow for a desirable flow or flow rate through the channel while having a narrow enough opening width that a surface tension across the opening prevents a gel from entering the channel. In some embodiments, the present invention features a microfluidic channel having sides which taper in from a base to provide an opening width which is smaller than the base. In another embodiment, the present invention features a crossover region between two microfluidic channels, wherein one of the channels has sides which taper in from a base to provide an opening width which is smaller than the base. As a non-limiting example, the crossover region may allow for a fluid medium to flow from a channel having tapered sides and also prevent a gel from flowing into the channel having tapered sides.

In one non-limiting example, the microfluidic system (100) may comprise: a first channel (110) configured to house cells; a second channel (210) which crosses the first channel (110) at a crossover region (120); and a communication pore (130) at the crossover region (120), the pore fluidly connecting the first channel (110) to the second channel (210) via an anastomosis (135), such that the first channel (110) is configured to receive a fluid medium from the second channel (210). In selected embodiments, the anastomosis (135) may be a vertical anastomosis or an anastomosis between an upper channel and a lower channel. As non-limiting examples, a vertical anastomosis may comprise a vertical or a horizontal communication pore (130) between the upper channel and the lower channel.

In some embodiments, the first channel (110) may be disposed within a first layer (105), the second channel (210) may be disposed within a second layer (205), and the second layer (205) may be bonded atop or below the first layer (105). In alternative embodiments, the second channel (210) may be embedded within the first channel (110) at the crossover region (120) such that the second channel (210) only fills a partial space inside the first channel (110) and does not occlude the entire channel, and wherein an embedded communication pore (130) comprises the anastomosis (135). In other alternative embodiments, the second channel (210) may be embedded within the first channel (110) at the crossover region (120) such that the second channel (210) fills a partial space inside the first channel (110) as to allow for continuous flow through the first channel (110) at the crossover region (120). In one embodiment, the first channel (110) may be a cell-containing channel which comprises a tissue chamber (112). In a further embodiment the tissue chamber (112) may be fluidly connected to another tissue chamber (112).

In selected embodiments, the system (100) may comprise multiple cell-containing channels, and wherein each cell-containing channel comprises a different cell population. In some selected embodiments, the different cell-containing channels may be aligned in parallel rows. As non-limiting examples, different cell populations may simulate different tissues, disease models, or organs. In one embodiment, different cancer cells or other diseased cells may be embedded within the system to provide an in vitro disease model. In another embodiment, different extracellular matrix types may be used for different cell types or applications. As a non-limiting example, fibrin may be used as an extracellular matrix which is later replaced by collagen secreted by fibroblasts. In some embodiments, the cells may be stem cells, inducible pluripotent stem cell-derived cells, progenitor cells, terminally differentiated cells, or a combination thereof. In some other embodiments the cells may be derived from blood, cardiac tissue, skeletal muscle tissue, liver tissue, pancreatic tissue, lung tissue, bone tissue, umbilical cord tissue, endothelial tissue, central nervous system tissue, gastrointestinal system tissue, endocrine tissue or cells, paracrine cells, enzyme secreting cells, progenitors thereof, or a combination thereof.

In a selected embodiment, the cells may undergo angiogenesis. In another embodiment, the second channel (210) may be fluidly and operatively connected to a pump. In yet another embodiment, the flow of the fluid medium in the second channel (210) may be pressure-driven. In still another embodiment, the fluid medium may be delivered from the second channel (210) to generate an interstitial flow through the first channel (110). According to one preferred embodiment, the first channel (110) may comprise a loading port for loading cells into the first channel (110). According to another preferred embodiment, the fluid medium may be supplied through the second channel (210) under a stable pressure drop from an inlet to an outlet.

The present invention may feature a microfluidic system (100) for forming a perfused capillary network. As a non-limiting example, the system may comprise: a first layer (105) comprising a plurality of cell channels embedded therein, each cell channel having a plurality of tissue chambers (112) disposed along said cell channel, the tissue chamber (112) being configured for housing cells, wherein the tissue chamber (112) has a width greater than a width of the cell channel, wherein the cell channels are arranged so as to be in parallel with each other and so that the tissue chambers (112) of one cell channel are aligned with the tissue chambers (112) of the neighboring cell channel, wherein the tissue chambers (112) of one cell channel are fluidly connected to the tissue chambers (112) of the neighboring cell channel; a second layer (205) comprising a plurality of medium channels embedded therein, the medium channels being aligned in parallel with each other, wherein the second layer (205) is bonded to the first layer (105) such that the medium channels are perpendicular to the cell channels; and a plurality of communication pores (130), each communication pore (130) being disposed at each intersection of the medium channels and the cell channels such that the communication pore (130) fluidly connects the medium channel to the cell channel such that cells in the tissue chambers (112) receive media from the medium channel, In one embodiment, the cell channels may be aligned in an x-direction, the medium channels may be aligned in a y-direction, and the communication pores (130) may be disposed in a z-direction. In one other embodiment, media may be delivered from the medium channels to the cell channels via the communication pores (130) to generate interstitial flow across the tissue chambers (112).

Tissue chambers of one cell channel may be fluidly connected to tissue chambers in a second (different) cell channel. The second layer (205) may comprise embedded medium channels (210) with inlets and outlets. The second layer (205) comprises one ora plurality of medium channels (210), e.g., 2, 3, 4, 5, 6, 7, 8, 9, 10, 11, 12, etc. The example shown in FIG. 1A comprises four medium channels (210); however, the present invention is not limited to the configuration shown in FIG. 1A. The medium channels (210) deliver media throughout the system (100), e.g., to the tissue chambers (112), the cell channels (110).

One or more communication pores (130) are disposed in the system (100). A communication pore (130) is a small area where a cell channel (110) (e.g., tissue chamber (112)) connects with a medium channel (210) (see FIG. 1B). Cells in the cell channel (110) (e.g., tissue chamber (112)) receive media from the medium channel (210) via the communication pores (130). FIG. 1B shows a cross-sectional view of a communication pore (130) as the medium flows from the second layer (205), in this case the upper layer, to the first layer (105). FIG. 1C is a side view showing vertical anastomosis (135) of endothelial cells (ECs) that seals the inner walls and forms the connections between medium channels and tissue chambers.

In further embodiments, the system may comprise a secondary interface. The secondary interface may comprise channels with inlets and outlets in the cell layer. These channels may be connected to the tissue chambers, and there may be pillars at the connection interface that prevent the gels from bursting into these channels.

Based on different materials loaded into the channels of the secondary interface during the tissue culturing, the secondary interface may have different functions. For example, if culture medium is loaded, the secondary interface may be used as side channels to deliver cancer cells and drugs into the vascular networks or the extracellular matrix. In some embodiments, by loading epithelial cells, the secondary interface may form an air/liquid interface to mimic lung functions on chip.

The interstitial flow of culture medium inside the cell-matrix (e.g., ECs, fibrin gel mixture) may be calculated by numerical simulation. Culture medium is delivered from the medium channels (210) to generate interstitial flow across all tissue chambers (112). FIG. 2A and FIG. 2B show a numerical simulation of media flow. FIG. 2A is a top view showing the interstitial flow for angiogenesis and anastomosis. FIG. 2B is a side view of a tissue chamber (of a cell channel (110)).

Figure 3B:
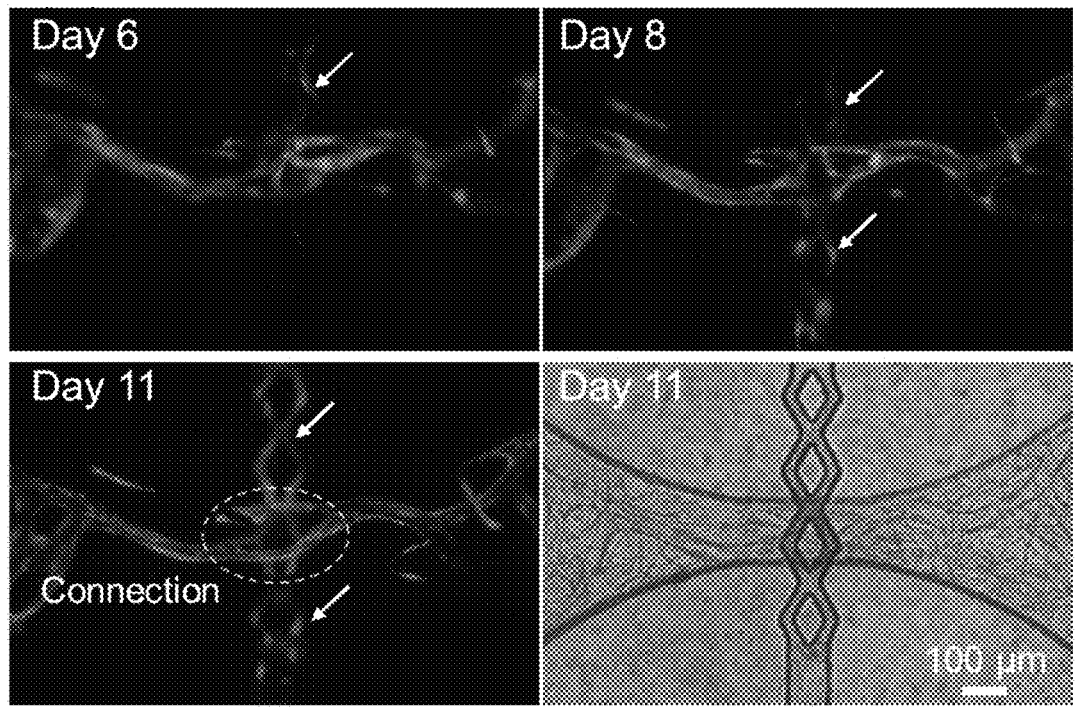
FIG. 3B shows the development of large-scale capillary networks (vertical anastomosis at the communication pore).

During experiments, ECs-fibrin gel mixture was loaded into tissue chambers (x-direction). After gel curing, laminin was injected into medium channels. Then, EGM-2 (Lonza)

culture medium was supplied through medium channels under a relatively stable pressure drop from inlets to outlets. As shown in FIG. 3A, after 11 days, capillaries in all of the nine chambers formed connected networks. The white arrows indicate the communication pores and the sites of vertical anastomosis (135). ECs grew vertically toward the medium channels, sealed the inner walls and formed connections between medium channels and tissue chambers (see FIG. 3B).

Figure 4A:
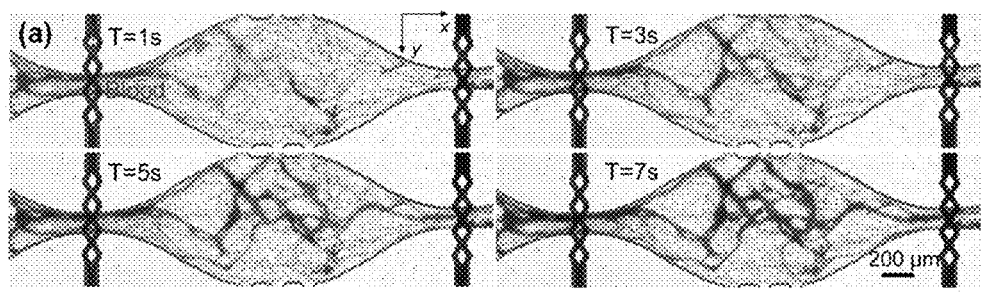
FIG. 4A shows blood perfusion in the x-direction in in vitro capillaries of the present invention.
Figure 4B:
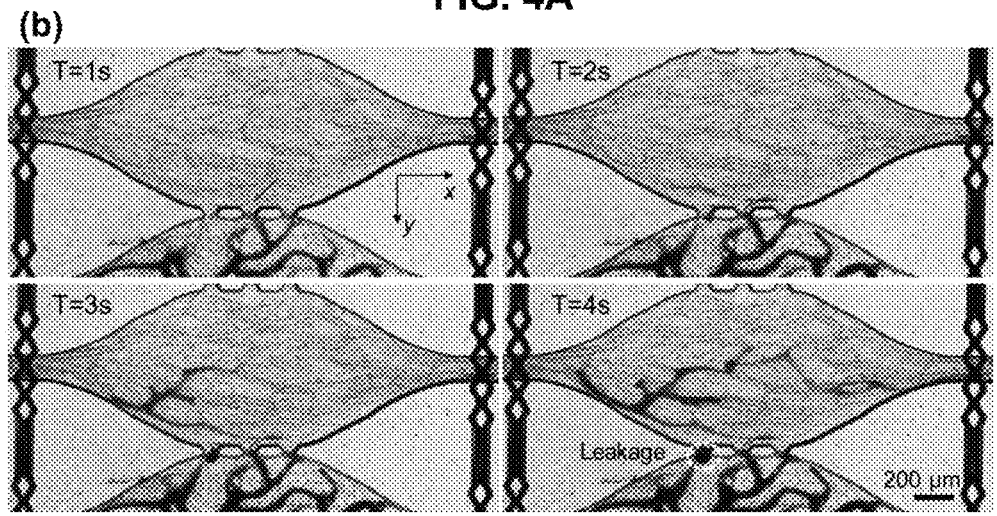
FIG. 4B shows blood perfusion in the y-direction in in vitro capillaries of the present invention.
Figure 4C:
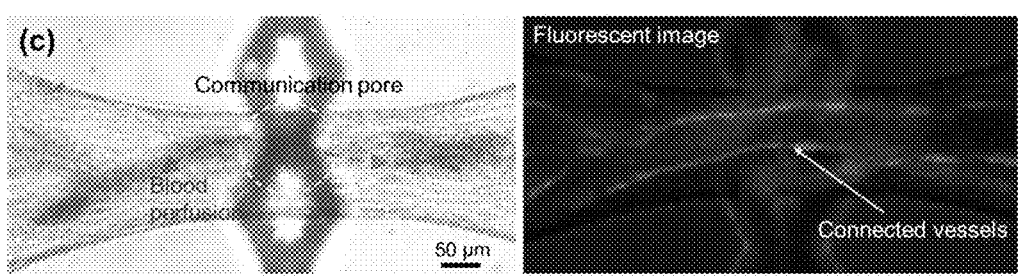
FIG. 4C shows development of the capillary networks and the vessel connections.

Blood perfusion (whole blood, 1:1 diluted with PBS buffer) was conducted using these in vitro capillaries to demonstrate their network connections. Blood flow was in both x-direction and y-direction (see FIG. 4A, FIG. 4B). Images at communication pores showed no leakage between medium channels and capillaries, confirming the vertical anastomosis (135) (see FIG. 4C).

Figure 5A:
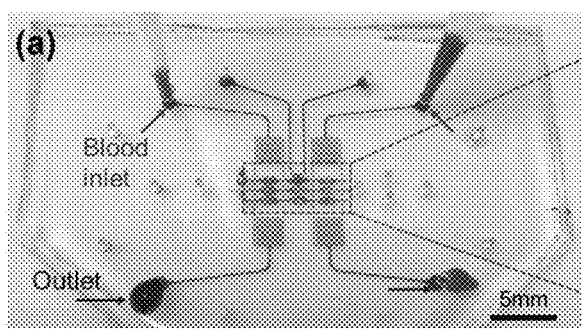
FIG. 5A shows a prototype of a system of the present invention.
Figure 5B:
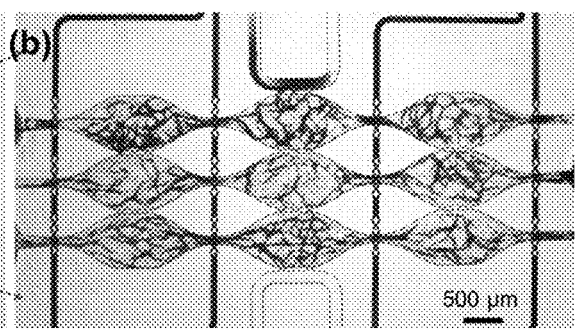
FIG. 5B shows development of large-scale capillary networks perfused by blood in the system of FIG. 5A.
Figure 6A:
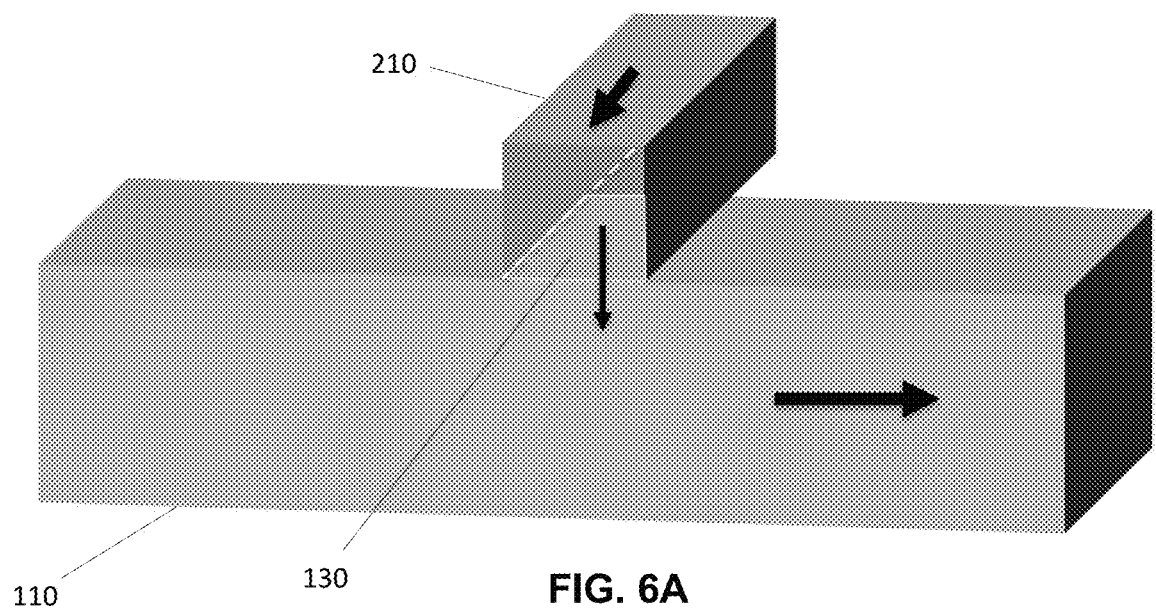
FIG. 6A shows a drawing of a communication pore forming a vertical anastomosis between a first channel and a second channel.
Figure 6B:
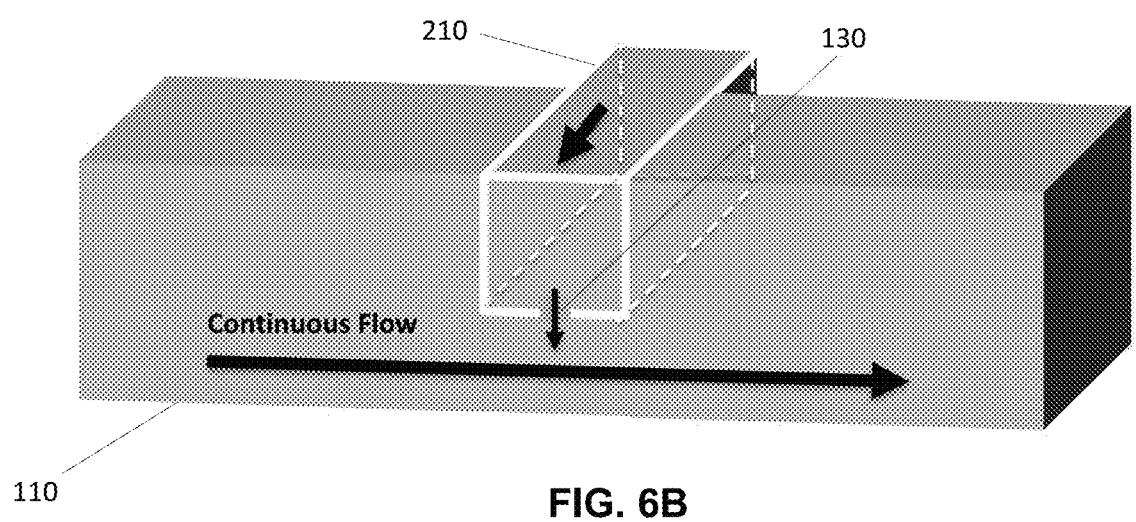
FIG. 6B shows a drawing of a communication pore forming a vertical anastomosis between a first channel and an embedded second channel.
Figure 6C:
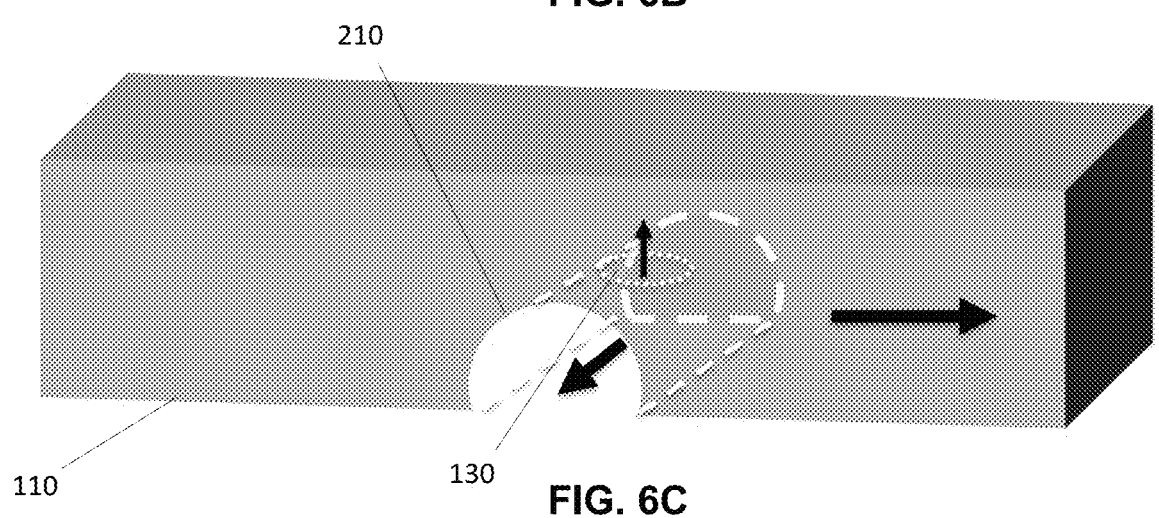
FIG. 6C shows a drawing of a communication pore forming a vertical anastomosis between a first channel and an embedded second channel.

FIG. 5A and FIG. 5B shows a prototype of a system of the present invention. Large-scale capillary networks perfused by blood were achieved.

Example 1

Example 1 describes the construction of a system of the present invention. The present invention is not limited to the methods, compositions, or configurations described in this example.

A system was constructed by bonding two layers of polydimethylsiloxane (PDMS). The PDMS-based device was constructed using a standard soft-lithography method with an SU8 master mold on a silicon substrate. Degassed PDMS pre-polymer mixture (mixed PDMS base with curing agent in a 10:1 ratio, Sylgard 184, Dow Corning, Inc.) was cast over the mold and baked overnight at 65° C. The cured PDMS with embedded channels was subsequently diced by scalpel and removed from the master mold. One inlet and one outlet were punched through the PDMS slab by a 1.5 mm hole-puncher, and then the PDMS slab was ready to be bonded with the PDMS membrane by oxygen plasma treatment. Medium channels in the upper layer and tissue chambers in the bottom layer were crossed after bonding (see FIG. 1A, FIG. 1B). The crossed areas are the communication pores.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A microfluidic system (100) comprising:
   a. a first layer (105) comprising a first channel (110) therein, the first channel (110) fluidly connected to a plurality of tissue chambers (112) which are configured to house cells;
   b. a second layer (205) above or below the first layer (105), the second layer (205) comprising a second channel (210) therein, the second channel (210) comprising:
      i. a first full-width region (212) and a second full-width region (212);
      ii. a first branch point (214) at an end of the first full-width region (212), a second branch point (214) at an end of a second full-width region (212), and a node (230) between the two branch points (214);
      iii. a plurality of branch channels (225) fluidly connecting the first branch point (214), the node (230), and the second branch point (214), wherein the branch channels (225) are disposed separately between the first branch point (214) and the node (230) and between the node (230) and the second branch point (214), and wherein the branch channels (225) recombine at each branch point (214) and at the node (230); and
      iv. a crossover region (120) in which the second channel (210) passes over or under the first channel (110) at a point upstream or downstream from one or more tissue chambers of the plurality of tissue chambers (112), the crossover region (120) comprising the node (230) and the branch channels (225) but not the full-width regions (212);
   c. a communication pore (130) forming a vertical anastomosis (135) between the first channel (110) and the second channel (210) in the crossover region (120);
   wherein the first layer (105) fluidly connects directly to the second layer (205) by the communication pore (130).

2. The system of claim 1, wherein the communication pore (130) is configured to prevent a gel from passing from the first channel (110) into the second channel (210).

3. The system of claim 1, wherein the branch channels (225) are narrow enough to prevent a gel from passing from the first channel (110) into the second channel (210).

4. The system of claim 1, wherein the communication pore (130) is configured to provide for a flow of a liquid medium from the second channel (210) to the first channel (110).

5. The system of claim 1, wherein the branch channels (225) are narrower than the full-width regions (212) of the second channel (210).

* * * * *